United States Patent [19]
Callan et al.

[11] Patent Number: 5,652,388
[45] Date of Patent: Jul. 29, 1997

[54] APPARATUS AND METHOD FOR DETECTING PRINTING PRESS WEB BREAKAGE

[75] Inventors: Ronald Callan, Lemont; Michael Gregory, Winfield; Tat Luk, Aurora; Gifford Neill, Hanover Park, all of Ill.

[73] Assignee: Baldwin Web Controls, Lombard, Ill.

[21] Appl. No.: 517,333

[22] Filed: Aug. 21, 1995

[51] Int. Cl.⁶ .................................................. G01N 29/10
[52] U.S. Cl. ............................. 73/628; 73/600; 73/159
[58] Field of Search ............................. 73/159, 599, 600, 73/628, 661; 364/469, 470, 471, 472

[56] References Cited

U.S. PATENT DOCUMENTS

| | | | |
|---|---|---|---|
| 3,807,868 | 4/1974 | Simila | 356/118 |
| 3,978,714 | 9/1976 | Shraiber et al. | 73/625 |
| 4,496,428 | 1/1985 | Wells | 73/159 |
| 4,519,249 | 5/1985 | Hunt | 73/159 |
| 4,612,807 | 9/1986 | Wunderer | 73/580 |
| 5,036,706 | 8/1991 | Gnuechted et al. | 73/597 |
| 5,280,724 | 1/1994 | Higo et al. | 73/624 |
| 5,378,918 | 1/1995 | Ötti | 250/571 |

FOREIGN PATENT DOCUMENTS

| | | |
|---|---|---|
| 0167010 | 1/1986 | European Pat. Off. |
| 2661749 | 11/1991 | France |
| 1385184 | 2/1975 | United Kingdom |

Primary Examiner—Hezron E. Williams
Assistant Examiner—Rose M. Miller
Attorney, Agent, or Firm—Morgan & Finnegan, L.L.P.

[57] ABSTRACT

An apparatus for detecting breakage of a web of material traversing a machine for feeding the web, and a method for the same. The apparatus includes a housing for mounting three transducers, a first transducer adapted to periodically emit a burst of energy for a period of time, the burst of energy being reflected off an object and producing an echo signal. A second transducer adjacent to the first transducer receives a portion of the echo signal, and a third transducer also adjacent to the first transducer receives another portion of the echo signal. The strongest portion of the echo signal is used to detect whether the web is broken.

24 Claims, 7 Drawing Sheets

APPARATUS AND METHOD FOR DETECTING PRINTING PRESS WEB BREAKAGE

TECHNICAL FIELD

This invention relates generally to non-contact measurement systems for monitoring a web of material, and, more particularly, to an ultrasonic apparatus and method for diagnosing printing press web breakage while minimizing the effect of web wrinkles on the detection process which utilizes an ultrasonic transmitter and at least two ultrasonic receivers.

BACKGROUND OF THE INVENTION

Measurement systems, particularly ultrasonic measurement systems, are widely used in the printing industry to monitor characteristics of a web of paper ("web") passing through machinery such as a printing press. Ultrasonic technology is popular because of its reliable operation in the often dusty and dirty printing plant environment.

The principles of operation of ultrasonic measurement systems are well-known. When ultrasonic energy (i.e., a frequency higher than the audible range, or above 20 kHz) is incident on an object such as a web, part of the energy is reflected, part is transmitted and part is absorbed. Measuring the time between transmission of the energy and return of the reflected energy (the "return echo"), makes it possible to determine the distance from the ultrasonic transmitter and/or receiver to the web.

One important function of an ultrasonic measurement system for a printing press is to detect web breaks by checking for the absence or presence of a web within a certain distance from the measurement system. A typical ultrasonic web break detection system generates an emergency shutdown signal if the web is determined to be absent. The web is judged to be absent when no return echo is received by an ultrasonic receiver within certain amount of time, or if the time for receipt of the return echo indicates that the web has traveled outside of acceptable tolerances. Conversely, if there is a return echo within an acceptable time, the measurement system considers the web to be present and does not generate an emergency shutdown signal.

When a web breaks, the web is often directed back into the printing press, where it becomes entangled in the press rolls, resulting in substantial down-time and repair expenses. When a web break is detected it is often desirable to deploy a press protection device which stops the printing presses and severs and/or re-directs the web at various points. Accordingly, a false web breakage alarm could cause significant and unnecessary delay and expense.

Two well known ultrasonic web break detection systems used in the printing industry include the sonic web break detector disclosed in U.S. Pat. No. 5,036,706 to Gnuechtel et. al. and the model 1127 ultrasonic web break detector manufactured by Baldwin Web Controls. Such systems detect the presence or absence of a web within certain tolerances which vary with the speed of the web.

Web break detectors generally mount directly to a printing press, perpendicular to the plane of the web, within a few inches of the web's surface. Known web break detectors typically comprise a pair of piezoelectric transducers functioning in opposite ways, i.e., one transducer transmits ultrasonic energy at a predetermined amplitude, frequency and phase angle and a second transducer receives a return echo of the transmitted energy. The transmitter transducer and the receiver transducer together comprise a sonic head, and are typically tilted toward each other at a slight angle, for example, 5 to 10 degrees.

The transmission and reception of sonic energy by the sonic head is typically coordinated by a controller module, which causes the transmitter to emit a short burst of sonic energy every few milliseconds and, if the web is present, looks for the receiver to detect a return echo of sonic energy within a certain time, for example 300 to 780 microseconds, after the beginning of the transmission of the energy burst.

In addition, when the web is present, the receiver must generally show the presence of a return echo from the web for a certain number of consecutive transmit signals. The number of absent return echo signals tolerated is dependent on web speed, and decreases as web speed increases. Thus, the number of return echo absences functions as a filter which helps to ameliorate the possibility of the detection system issuing an emergency shutdown signal because of web flutter or small holes in the web.

Further, if a web is present, the controller module may continuously monitor the strength of the return echo to determine whether the receiver transducer has become dirty—covered with ink or paper dust, for example. A two-transducer sonic head will not function properly if the receiver transducer is too dirty.

Often, a single controller synchronizes multiple web break detection systems, each detection system having one or more sonic heads, so that the timing of sonic energy transmission and reception for each sonic head is synchronized. Synchronizing detection systems which are in close proximity to each other eliminates interference in the detection of return echoes which would result if timing were not precisely synchronized.

Typical ultrasonic web break detection systems utilizing a single transmitter-receiver transducer pair per sonic head suffer from the problem of mistaking harmless web angles and wrinkles in the web, which cause marked degradation of the return echo signal, for actual web breaks, thereby shutting down machinery and severing and redirecting webs unnecessarily.

Past systems have attempted to solve the false web breakage alarm problem caused by wrinkles by connecting the processed signals from two sonic heads in parallel logic, so that each sonic head must detect the absence of the web before an emergency shutdown signal is generated.

Parallel logic connection of the sonic heads suffers from various disadvantages, however. First, space within a detection system is wasted with two sonic heads essentially functioning as one detection unit. Second, cost and complexity are increased, where one transmitter transducer and associated electronics must be utilized for each receiver transducer, then both transmitter transducers must be synchronized to prevent interference between the adjacent transducer pairs. Third, the controller module must perform the same web detection analysis for each receiver transducer input. This wastes controller inputs and increases web break detection times, thus creating the potential for more serious press jams. For example, when two sonic heads are connected in parallel, a small web tear at only one edge (i.e., under only one sonic head), often referred to as an "edge tear", will not result in press shutdown until the tear travels further across the web. This is because, when connected in parallel logic, both sonic heads must detect a web break before an emergency shutdown signal is generated.

Accordingly, one object of the invention is to minimize false web breakage alarms resulting primarily from web wrinkles and secondarily from angular web distortions.

Another object is to reduce a number of components necessary to detect web breakage and prevent false web breakage alarms resulting from web wrinkles.

A further object is to increase reliability of web breakage detection systems.

A still further object of the invention is to decrease web tear detection time.

SUMMARY OF THE INVENTION

According to the present invention, the foregoing objects and advantages are attained by a method of minimizing an effect of a web wrinkle during web break detection including periodically transmitting a burst of energy for a period of time, the burst of energy being reflected off the web and producing an echo signal; receiving a portion of the echo signal by a first transducer and a second transducer; determining strengths of the portions of the echo signal received by the first and second transducers; comparing the strengths to determine which portion of the echo signal is stronger; and analyzing the strongest echo signal to determine the presence of a web break.

In accordance with another embodiment of the present invention, an apparatus for detecting a position of a web of material traversing a machine for feeding the web comprises a housing for storing three transducers; a first transducer adapted to periodically emit a burst of energy for a period of time, the burst of energy being reflected off an object and producing an echo signal; a second transducer adjacent to the first transducer, adapted to receive a portion of the echo signal; and a third transducer adjacent to the first transducer, adapted to receive another portion of the echo signal.

Other objects and advantages of the present invention will become readily apparent to those skilled in the art from the following description of the preferred embodiment of the invention which has been shown and described by way of illustration, as the best mode contemplated of carrying out the invention. As will be realized, the invention is capable of other and different embodiments, and its details are capable of modifications in various obvious respects, all without departing from the invention. Accordingly, the drawings and description are to be regarded as illustrative in nature, and not as restrictive.

BRIEF DESCRIPTION OF THE DRAWINGS

FIGS. 4 and 4A–4C are a schematic electrical diagram of the ultrasonic detection module according to the preferred embodiment of the present invention.

DETAILED DESCRIPTION OF THE PREFERRED EMBODIMENT

Figure 1:
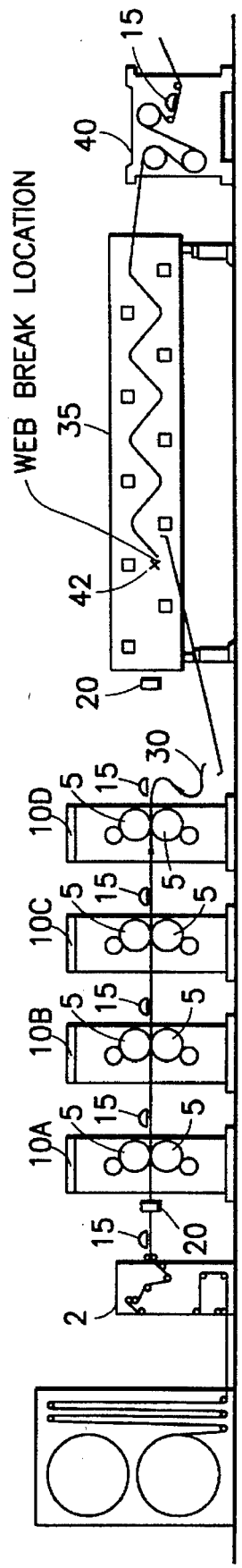
FIG. 1 illustrates a typical multiple printing unit heat set press system.

Turning now to the drawings, wherein like numerals designate like components, FIG. 1 illustrates a typical multiple printing unit heat set press system. As shown, the press may include multiple printing units 10A–10D, each having one or more blanked impression cylinder combinations 5 employed in the printing process. When the printing units 10A–10D are running, the blanked cylinders 5 feed a continuous paper web 30 through the printing units 10A–10D, from an infeed unit 2 upstream from the printing units 10A–10D and then through a web dryer unit 35 and a chill unit 40 downstream of the printing units 10A–10D.

Web break detection systems 15, which may be ultrasonic systems, are located at various points in the system above web 30 to detect when the web 30 breaks. As shown, a web break 42 has occurred in the dryer unit 35.

FIG. 2a illustrates a cut-away side view of an ultrasonic detection module 50 for diagnosing printing press web breakage according to the preferred embodiment of the present invention. The detection module 50 may be molded plastic, and have dimensions of approximately 4.5 inches long by approximately 1.7 inches high.

The detection module 50 may be adjustably located in a detector bar 130, as illustrated in FIG. 2b, which may be extruded aluminum. The detector bar 130 may have a channel 132 sufficiently long to hold up to four detection modules 50 arranged in series logic in slot positions 134a, b, c and d, respectively. Stocking the detector bar with four modules 50 allows for accurate web detection at both full and half-web conditions. The detector module 50 has approximately the same dimensions as a Baldwin model 1127 sonic head, and thus slots 134a, b, c or d may house either detector modules 50 or prior sonic heads such as the Baldwin 1127 model.

Referring again to FIG. 2a, a flange 51 may facilitate the insertion and removal of detection module 50 to and from the detector bar 130. A base side 58 of the detector module 50 fits into the detector bar channel 132. The detector bar 130 is mounted to a printing press via brackets (not shown) such that a detection side 60 of the detector module 50 is oriented toward the web 136, perpendicular to the plane of the web, nominally about 2.5 inches from the web's surface.

Three dimensionally-identical piezoelectric transducers 62, 64 and 66 are housed within individual transducer housings 52, 54 and 56. The transducers 62, 64 and 66 may be cylindrical, the center of each transducer being approximately 1.2 inches from its neighbor, and may be composed of a can containing a piezoceramic-driven aluminum membrane. Each can may in turn be encased in a rubber boot.

Suitable transducers are commercially available from Motorola, product numbers KSN6541A and KSN6540A and from S. Square Enterprise Co., Ltd., Taiwan, Product Nos. RE455ET/R180 or RE400ET/R180. A transducer which oscillates at 45.5 kHz, 40 kHz or another frequency may be utilized.

A transmitter transducer 62 may reside in transducer housing 52, held in place by transducer supports 52a and 52b. The transmitter transducer 62 may emit a short burst of four pulses, for example 77 microseconds long, of 45.5 kHz sonic energy toward the web every 10 milliseconds.

One receiver transducer 64 may reside in transducer housing 54 supported by transducer supports 54a and 54b, while a second receiver transducer 66, which is approximately 2.4 inches from the first receiver transducer, may reside in transducer housing 56, secured by transducer supports 56a and 56b. The receiver transducers 64, 66 detect the presence of a return echo of the transmitted sonic energy.

The transmitter transducer 62 is generally perpendicular to the plane of the web, while the receiver transmitters 64, 66 may be tilted toward the transmitter transducer 62 at a slight angle, for example, 10 degrees. Three cone-shaped horns 53, 57 and 59, which may be integral with the molded plastic of the detection module 50, counteract cross-talk between the transducers 62, 64 and 66. The center horn 57 associated with the transmitter transducer 62 is shorter than horns 53 and 59 associated with the receiver transducers 64, 66 so that, among other things, transmitted sonic energy radiates a wide beam. The beam width may be approximately 60 degrees, whereas past two-transducer sonic heads having angled transmitter transducers emitted total beam widths of only 45 degrees.

The receiver transducers 64, 66 are typically immediately active upon transmission of a burst of sonic energy by the transmitter transducer 62. To detect the presence of the web, a receiver transducer 64, 66 generally must detect a leading edge of a return echo of the transmitted sonic energy from 300 to 780 microseconds after initial transmission of the sonic energy toward the web.

Measuring the amount of time elapsed between initial transmission of sonic energy by the transmitter transducer 62 and detection of the leading edge of the return echo by the receiver transducer 64, 66, and knowing the speed of sound in air, makes it possible to calculate the distance of the web from the detection module 50. This calculation may be performed by a system controller (not shown) such as the Baldwin Web Controls model 1127 controller using well-known methods. The web is considered present if it is found to be within certain distances, for example, 1 to 4 inches, from the detection module 50. If the web is not detected within 1 to 4 inches of the module 50, an emergency shutdown signal is sent to the printing presses (depicted in FIG. 1) by the web system controller (discussed further below).

Connector port 55 allows the detector module 50 to be remotely connected to the system controller via a cable (not shown), which supplies communication between the detection module 50 and the system controller.

The system controller is responsible, for example, for (1) generating control signals which cause the transmitter transducer 62 to periodically emit bursts of sonic energy, (2) accepting and analyzing the return echo signals detected by the receiver transducer 64, 66, and (3) for determining whether the web is or is not present beneath the detector module 50 based on the analysis performed on the return echo signals.

A web is considered to be absent by the controller when there are no return echo signals from the web (within a given distance, such as 1 inch to 4 inches) for a certain number of consecutive transmit signals, the number of tolerated return echo absences being dependent on web speed. The methods for processing return echo signals based on web speed to determine web presence or absence are well-known to those skilled in the art.

Figure 2:
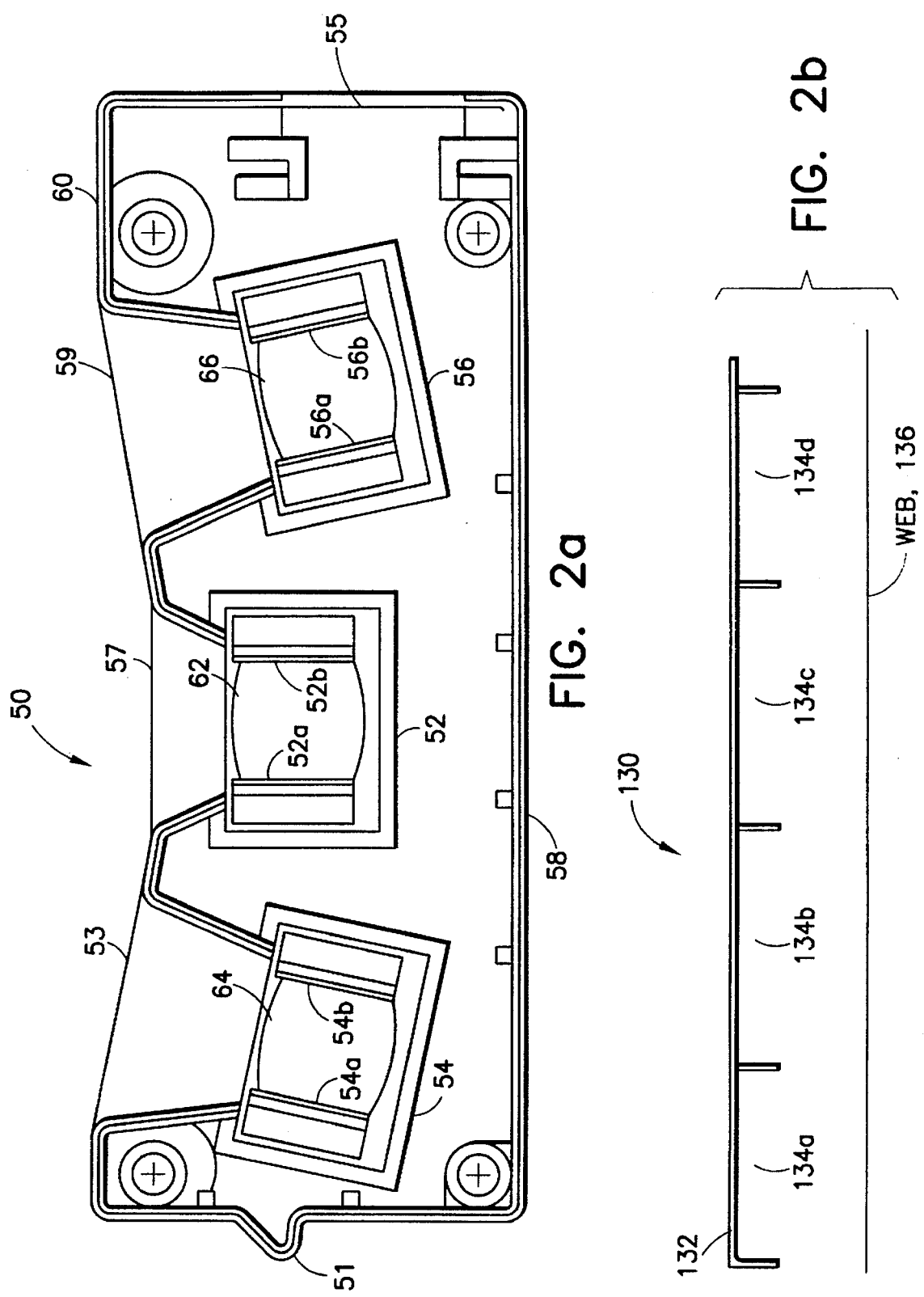
FIG. 2a illustrates a cut-away side view of an ultrasonic detection module for diagnosing printing press web breakage according to the preferred embodiment of the present invention.
FIG. 2b illustrates a cut-away side view of a detector bar for housing up to four detection modules according to the preferred embodiment of the present invention.
Figure 3:
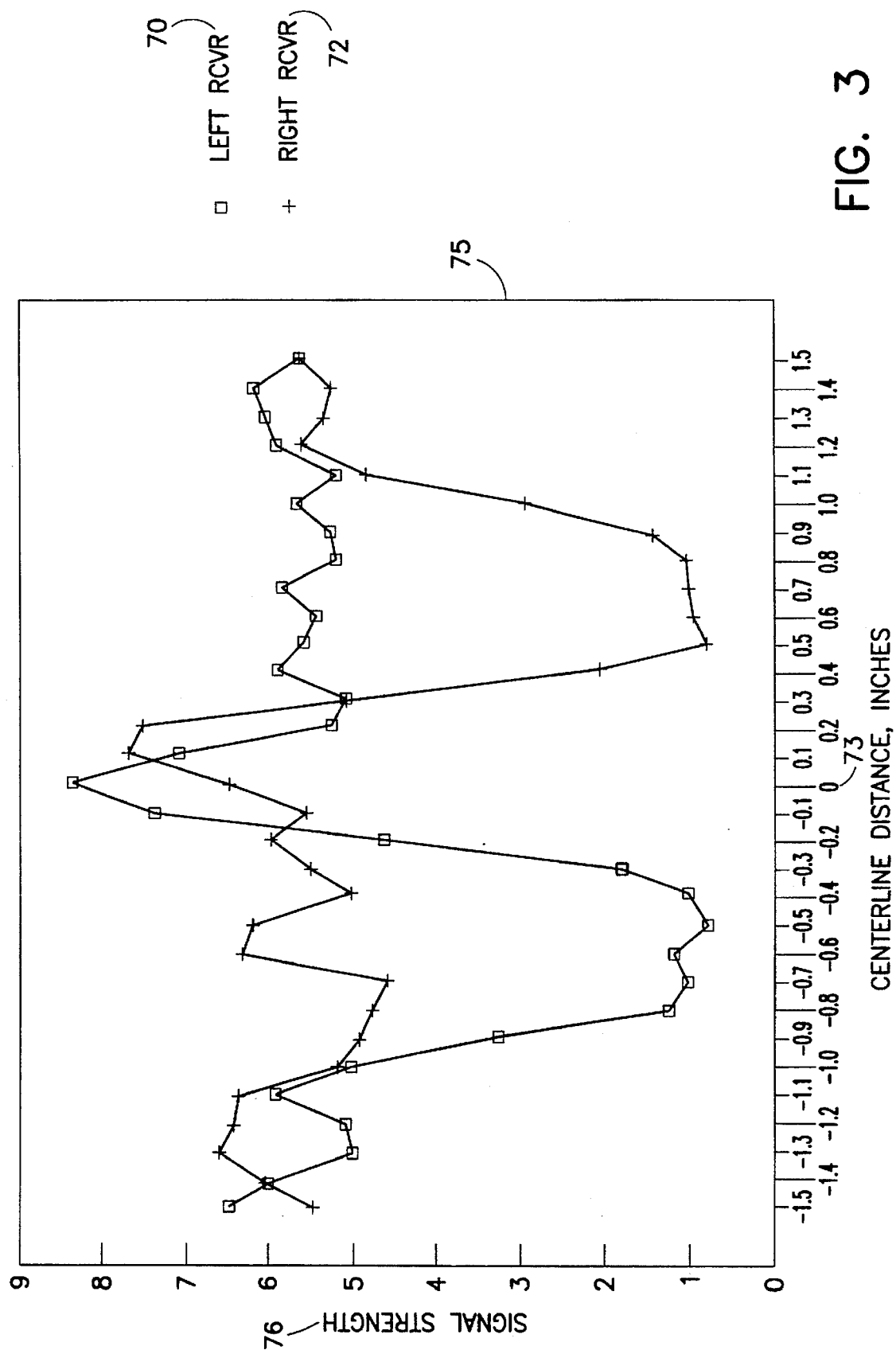
FIG. 3 illustrates the principle of operation of the ultrasonic detection module for diagnosing printing press web breakage while reducing false web break alarms according to the preferred embodiment of the present invention.

The frequency of false web break alarms which occur because of web wrinkles is reduced by using the preferred embodiment of the detection module constructed and oriented as described in connection with FIG. 2, the principle of operation of which is graphically illustrated in FIG. 3.

Return echo signal strength 75, i.e., a direct current magnitude of a return echo signal, is plotted against wrinkle distance from a centerline point 73 directly beneath a transmitter transducer, for both a left receiver transducer 70 and a right receiver transducer 72, the left and right receiver transducers being positioned approximately 2.4 inches apart, as a web wrinkle with a height of 0.43 inches passes from left to right under the ultrasonic detection module.

The graph 75 demonstrates that the left and right transducer receivers in different locations from the same transmitter have signal losses (and therefore absent return echo signals) as the wrinkle changes position. For example, while the right receiver transducer 72 maintains a relative signal strength of about 5.5 when the wrinkle is near the left of the detection module, the left receiver transducer signal strength drops to about 1. Conversely, as the wrinkle travels toward to the right side of the detection module, the left receiver transducer maintains a signal strength of approximately 5.5, while the right receiver transducer signal strength drops to about 1.

A similar situation results when the web is tilted side-to-side, and, as will be appreciated by one skilled in the art, the principles of the present invention which apply to reducing false web break alarms resulting from web wrinkles are also applicable to reducing the false alarms which occur because of web angles.

The loss of signal detected by the receiver transducer nearest to the wrinkle may explained by, for example, two general principles of wave mechanics. First, a rise in the web height because of the wrinkle creates an obstruction in the path of the return echo signals—the wrinkle thus blocks most of the return echo signals from being detected by the receiver transducer closest to the wrinkle. Second, the wrinkle causes a phase angle of the return echo signals to shift such that signal cancellation with the transmitted sonic energy results.

Thus, it is seen that the effect of web wrinkles on the web break detection process may be reduced by comparing the return echo signal strengths detected by the left and right receiver transducers prior to the system controller performing analysis of the return echo signals. Then, only the stronger of the left or right receiver transducer signal must be analyzed by the controller to determine whether the web is or is not present beneath the detector module.

The use of two receiver transducers in the manner described herein increases detector module reliability over prior systems having one transmitter transducer and one receiver transducer. For example, one receiver transducer which breaks or becomes blocked by dirt will not affect the continued operation of a detector module according to the present invention because a second receiver transducer will continue to detect web breaks in a manner comparable to prior two-transducer systems.

As will further be recognized by one skilled in the art, the three-transducer detector module according to the present invention eliminates the need for parallel logic connection of detection modules. Thus, web edge tears are quickly detected.

Figure 4A:
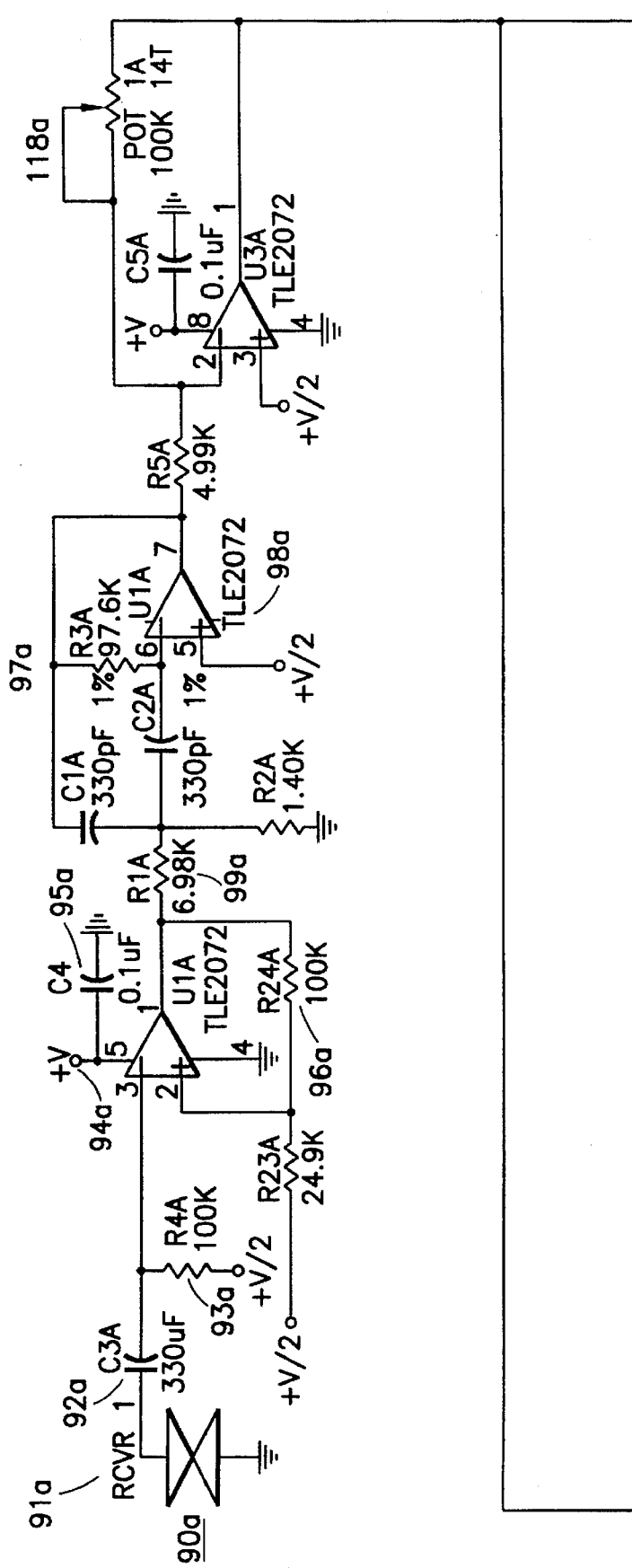
Figure 4B:
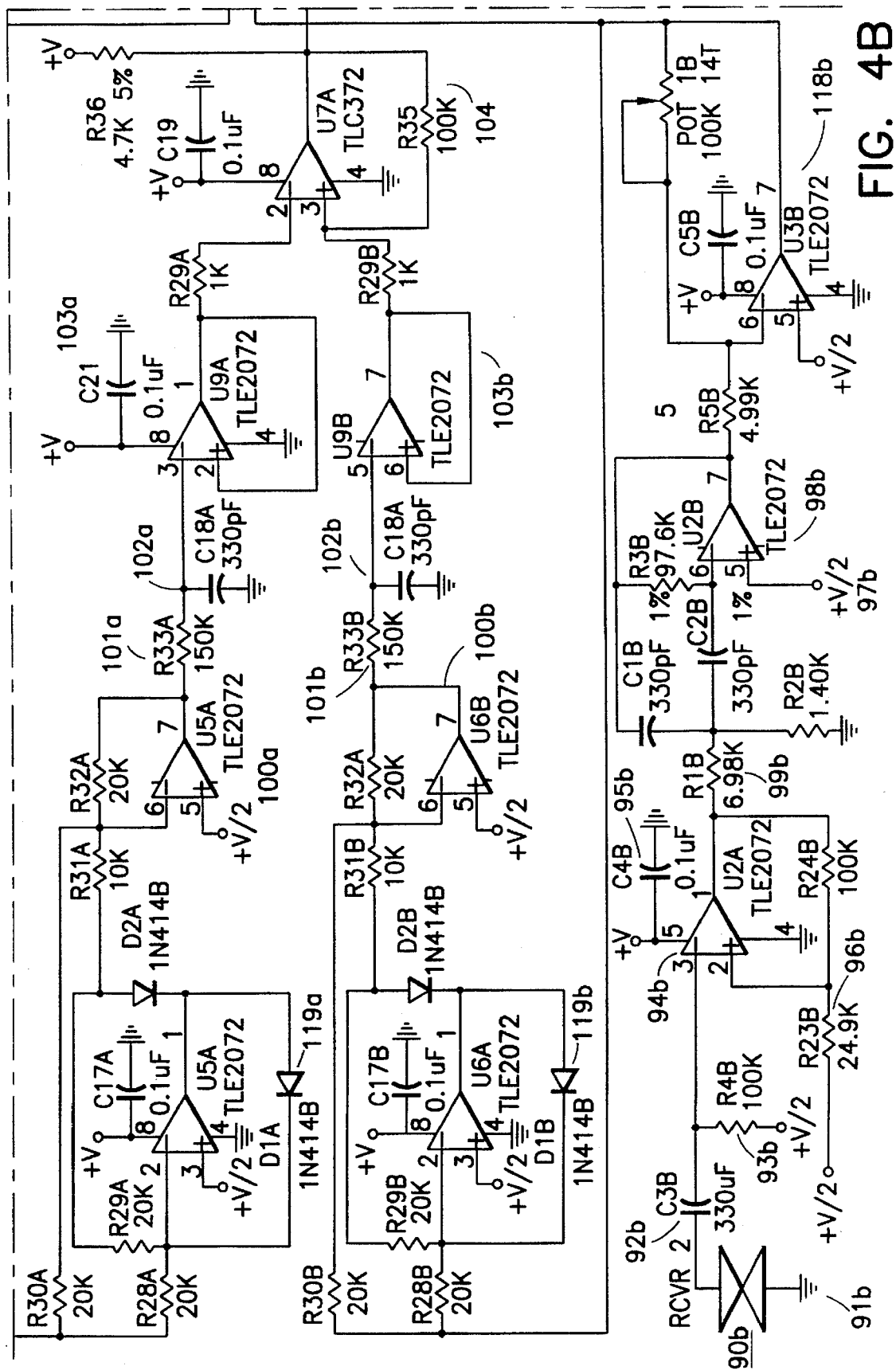
Figure 4C:
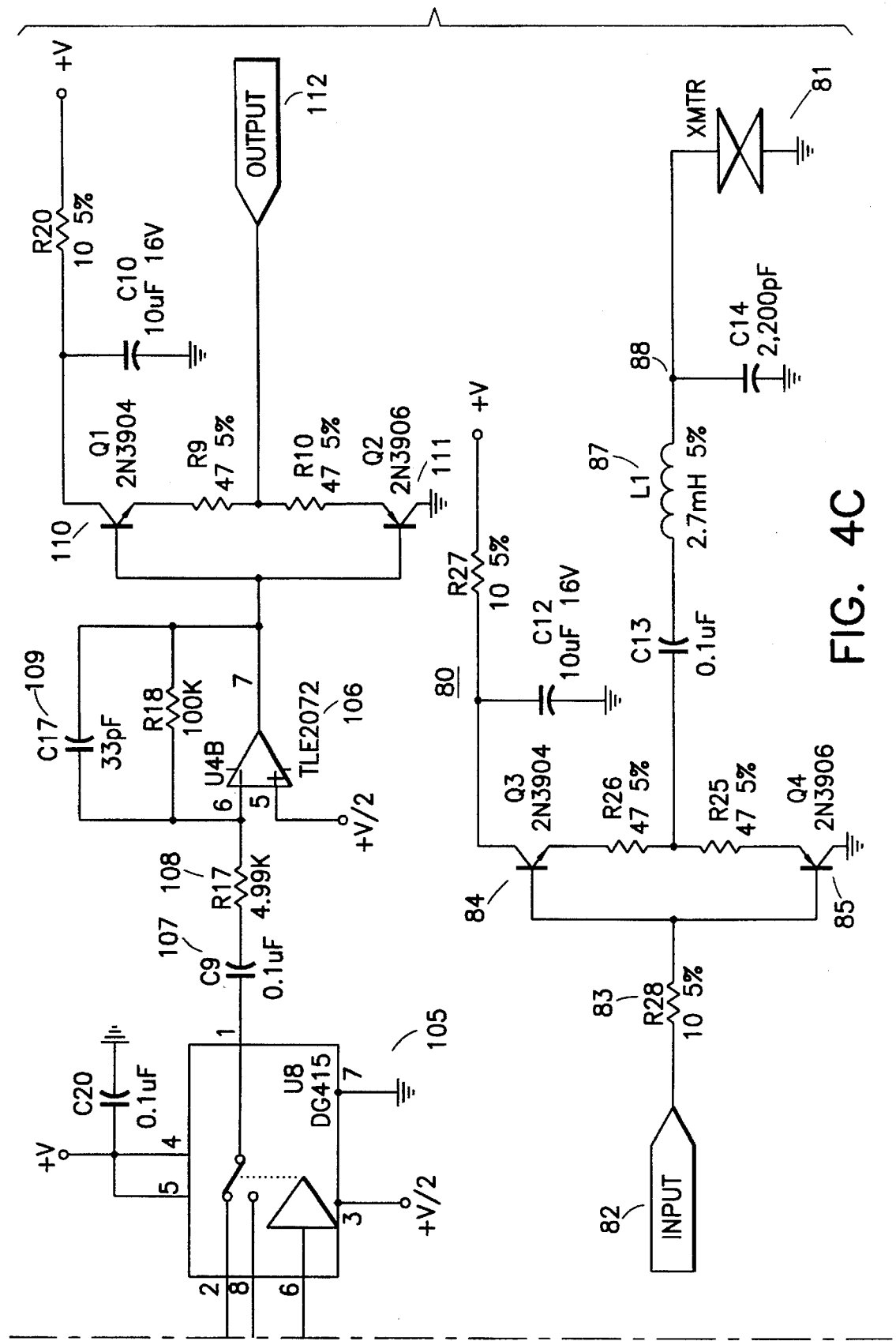

FIG. 4 is a schematic electrical diagram of the ultrasonic detection module according to the preferred embodiment of the present invention. The electronics are designed to be used with a Baldwin Web Controls model 1127 system controller, which utilizes well-known methods for providing a 4-pulse signal to a transmitter transducer, and for digitally processing the return echo signals detected by a receiver transducer.

Circuitry 80 associated with the transmitter transducer 81 of the preferred embodiment of the detection module described in connection with FIG. 2 receives an input 82 from the system controller (not shown) and is fed via resistor 83 to dual emitter followers 84, 85. The dual emitter followers 84, 85, via coupling capacitor 86 drive the transmitter transducer 81 at its low impedance resonance point, series resonating with inductor 87 and capacitor 88.

Circuitry 90a is associated with a first receiver transducer 91a, and identical circuitry 90b is associated with a second receiver transducer 91b, both transducers 91a and 91b being constructed and oriented according to the preferred embodiment of the detection module described in connection with FIG. 2.

The inputs from receiver transducers 91a,b are fed to capacitors 92a,b and resistors 93a,b. The capacitor-resistor combinations discriminate against lower frequency interference. Operational amplifier stages 94a,b, along with their associated capacitors 95a,b and resistors 96a,b, provide some gain along with impedance transformation. Stages 97a,b including operational amplifiers 98a,b and their associated components beginning with resistors 99a,b comprise two-pole bandpass filters centered at the transmitter transducer's frequency. Stages 97a,b also provide gain. The outputs of stages 97a,b serve as inputs to stages 118a,b, which provide large, adjustable gain.

Figure 5:
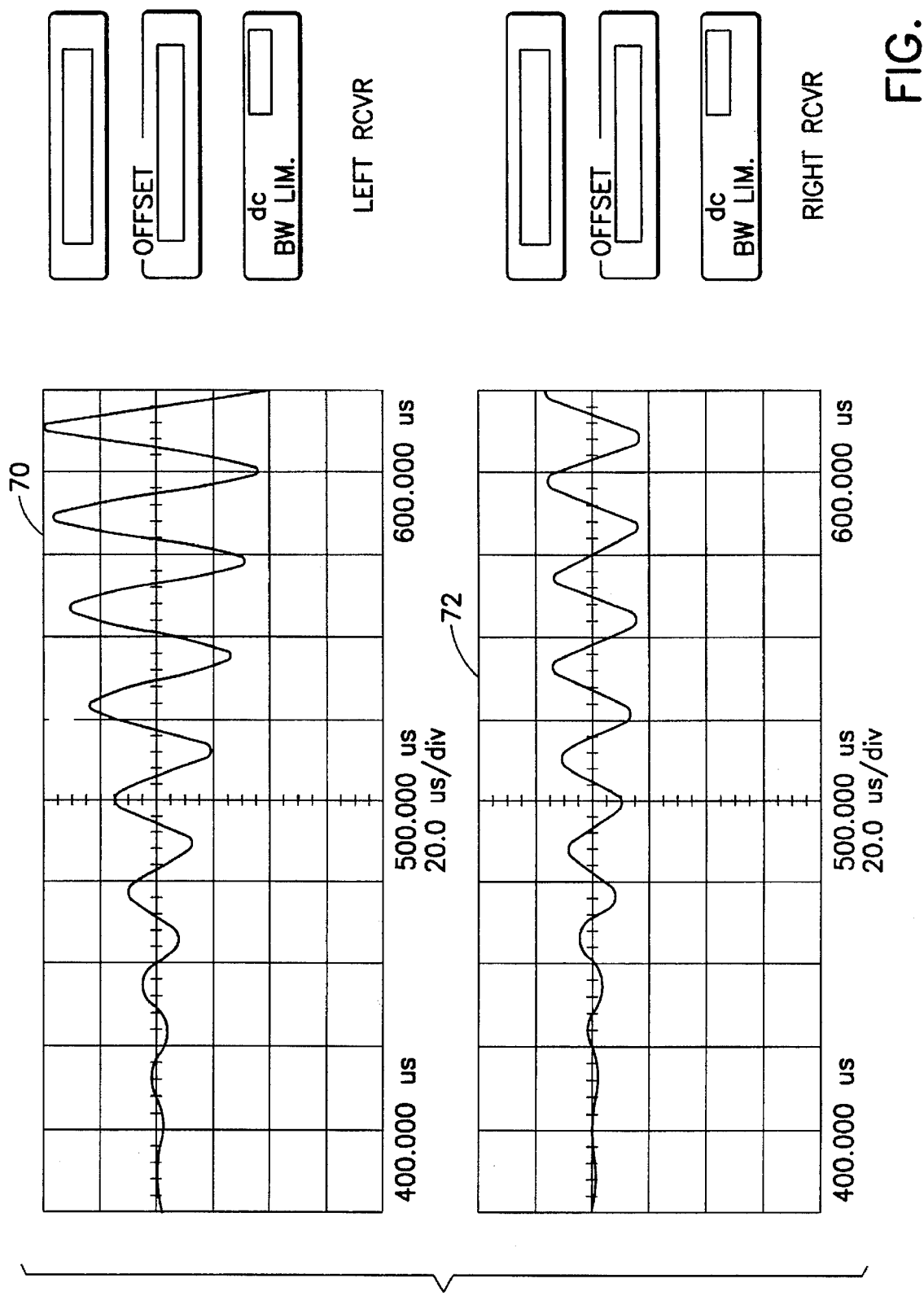
FIG. 5 illustrates the difference in phase angle of a return echo signal received by a left receiver transducer and a return echo received by a right receiver transducer of a detection module according to the preferred embodiment of the present invention.

At this point, the return echo-signals detected by each receiver transducer could be added together and processed by the system controller. The addition method is not preferred, however, because, as illustrated in FIG. 5, the signals from the left receiver transducer 70 and the right receiver transducer 72 may be out of phase. As shown, the signals are 180 degrees out of phase, so that simple addition of the signal magnitudes would be impossible, and could lead to unsatisfactory web detection.

Thus, it is preferred that stages 119a,b plus 100a,b perform full-wave rectification of the signals, so that absolute magnitudes or direct current values of the return echo signals detected by each receiver transducer are obtained. The rectified signals represent the relative strengths of the signals. Components 101a,b and 102a,b provide filtering.

The rectified and filtered signals are impedance transformed by operational amplifier stages 103a,b and their associated components. Then, each signal is fed into a comparator stage 104, which drives analog switch 105. The analog switch 105 selects the stronger of the two signals. The strongest signal is fed to a final amplifier stage 106 via capacitor 107 and resistor 108. Capacitor 109 provides stabilization. Stage 106 drives dual emitter followers 110, 111, the output 112 of which is capable of driving long cables (not shown) for connecting the detection module to the system controller.

It will be apparent that other and further forms of the invention may be devised without departing from the spirit and scope of the appended claims, it being understood that this invention is not to be limited to the specific embodiments shown.

We claim:

1. A method of minimizing an effect of a web wrinkle during web break detection, comprising:
   transmitting periodically a burst of energy for a period of time, the burst of energy being reflected off the web thereby producing an echo signal;
   receiving a first portion of the echo signal by a first transducer;
   receiving a second portion of the echo signal by a second transducer;
   determining a strength of the first portion of the echo signal and a strength of the second portion of the echo signal;
   comparing the strength of the first portion of the echo signal with the strength of the second portion of the echo signal to determine which portion is stronger; and
   analyzing the stronger portion of the echo signal to determine the presence of a web break.

2. A method for detecting a position of a web according to claim 1, further comprising the step of:
   sending an emergency shutdown signal to a machine feeding the web if the analysis determines that a web break is present.

3. A method for detecting a position of a web, comprising:
   transmitting periodically a burst of energy for a period of time, the burst of energy being reflected off the web thereby producing an echo signal;
   receiving a first portion of the echo signal by a first transducer;
   receiving a second portion of the echo signal by a second transducer;
   determining a strength of the first portion of the echo signal and a strength of the second portion of the echo signal;
   comparing the strength of the first portion of the echo signal with the strength of the second portion of the echo signal; and
   calculating an amount of time elapsed between transmission of the burst of energy and receipt of the portion of the echo signal by the transducer which received the strongest echo signal, thereby detecting whether the web position is acceptable.

4. A method of minimizing an effect of a web wrinkle or angular distortion during web break detection, comprising:
   transmitting periodically a burst of energy for a period of time, the burst of energy being reflected off the web thereby producing an echo signal;
   receiving a first portion of the echo signal by a first transducer;
   receiving a second portion of the echo signal by a second transducer;
   adding the first portion of the echo signal and the second portion of the echo signal to arrive at a resultant signal; and
   analyzing the resultant signal to determine the presence of a web break.

5. An apparatus for detecting a web break, comprising:
   a first transducer for periodically emitting a burst of energy for a period of time, the burst of energy being reflected off of the web thereby producing an echo signal;
   a second transducer adapted to receive a first portion of the echo signal; and
   a third transducer adapted to receive a second portion of the echo signal;
   a comparator in communication with said second transducer and said third transducer for determining whether the first portion of the echo signal or the second portion of the echo signal is stronger, and
   a controller in communication with said communicators which utilizes the stronger portion of the echo signal to detect whether the web is broken.

6. An apparatus for detecting a web break according to claim 5, wherein said first transducer comprises a piezoelectric transducer.

7. An apparatus for detecting a web break according to claim 5, wherein said first transducer is located perpendicular to a plane of the web.

8. An apparatus for detecting a web break according to claim 5, wherein said first transducer is located 2.5 inches from a normal operating position of the web.

9. An apparatus for detecting a web break according to claim 5, wherein the burst of energy emitted by said first transducer has a frequency of 45.5 kHz.

10. An apparatus for detecting a web break according to claim 9, wherein the burst of energy emitted by said first transducer lasts for seventy-seven microseconds.

11. An apparatus for detecting a web break according to claim 10, wherein the burst of energy emitted by said first transducer is repeated every ten milliseconds.

12. An apparatus for detecting a web break according to claim 5, wherein said second and third transducers comprise piezoelectric transducers.

13. An apparatus for detecting a web break according to claim 5, wherein said second and third transducers are angled toward said first transducer by ten degrees.

14. An apparatus for detecting a web break according to claim 5, further comprising:

a housing for maintaining said first, second and third transducers in a fixed relationship relative to each other.

15. An apparatus for detecting a web break according to claim 14, wherein said housing comprises molded plastic.

16. An apparatus for detecting a web break according to claim 14, wherein said housing further comprises:

a first conical cavity associated with an emission side of said first transducer;

a second conical cavity associated with a reception side of said second transducer; and a third conical cavity associated with a reception side of said third transducer, wherein said conical cavities reduce signal interference between said transducers and shape their ultrasonic beams.

17. An apparatus for detecting a web break according to claim 16, wherein said conical cavity associated with said first transducer is shorter than said conical cavities associated with said second and third transducers, so that the burst of energy emitted by said first transducer is wide enough that the portions of the echo signal are received by both said second and said third transducers simultaneously.

18. An apparatus for detecting a web break according to claim 5, further comprising:

a controller in communication with said first, second and third transducers for calculating an amount of time elapsed between transmission of the burst of energy and receipt of the strongest portion of the echo signal.

19. An apparatus for detecting a web break according to claim 18, wherein the web is unbroken if the strongest portion of the echo signal is detected within 250 to 1000 microseconds after the burst of energy is emitted.

20. An apparatus for detecting a position of a web of material traversing a machine for feeding the web, comprising:

a housing adapted to receive three transducers;

a first transducer disposed in said housing, adapted to periodically emit a burst of energy for a period of time, the burst of energy being reflected off an object thereby producing an echo signal;

a second transducer disposed in said housing adjacent to said first transducer, said second transducer adapted to receive a first portion of the echo signal;

a third transducer disposed in said housing adjacent to said first transducer, said third transducer adapted to receive a second portion of the echo signal; and an analyzer disposed in communication with said second and third transducers, said analyzer adapted to receive and compare said first and said second portions of the echo signal to determine the stronger portion of the echo signal and the presence of a web break.

21. An apparatus for detecting a position of a web, comprising:

a controller;

an ultrasonic transmitter in communication with the controller for periodically emitting a burst of sonic energy for a period of time in response to a control signal from the controller, the burst of sonic energy having a predetermined amplitude, frequency and phase angle and being reflected off the web thereby producing an echo signal, the echo signal having an amplitude, frequency and phase angle determined by a speed and position of the web;

a plurality of ultrasonic receivers, each of said plurality of receivers detecting a portion of the echo signal reflected toward each receiver;

means for determining relative strengths of the portions of the echo signal detected by each of said plurality of receivers; and means for transmitting to said controller a signal comprising the strongest portion of the echo signal detected by one of said plurality of receivers, wherein said controller calculates an amount of time elapsed between transmission of the burst of sonic energy and receipt of the signal comprising the strongest portion of the echo signal detected by one of said plurality of receivers, thereby detecting whether the web position is acceptable.

22. The apparatus of claim 20 wherein at least a portion of said analyzer is disposed in said housing.

23. The apparatus of claim 20 wherein said analyzer comprises a comparator.

24. The apparatus of claim 20 wherein said analyzer comprises a processor.

* * * * *